(12) United States Patent
Mori et al.

(10) Patent No.: US 6,255,061 B1
(45) Date of Patent: Jul. 3, 2001

(54) ANALYTICAL ELEMENT FOR THE ANALYSIS OF WHOLE BLOOD

(75) Inventors: Toshihiro Mori; Takaki Arai; Yoshikazu Amano, all of Asaka (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/464,613

(22) Filed: Dec. 15, 1999

(30) Foreign Application Priority Data

Dec. 15, 1998 (JP) .................................... 10-356065

(51) Int. Cl.[7] ............... C12Q 1/54; C12Q 1/60; C12Q 1/00; C12M 1/34; G01N 33/53

(52) U.S. Cl. ................. 435/14; 435/28; 435/11; 435/4; 435/283.1; 435/287.1; 435/288.7; 435/966

(58) Field of Search .................... 435/14, 28, 11, 435/4, 283.1, 287.1, 288.7, 966

(56) References Cited

U.S. PATENT DOCUMENTS 5,304,467 * 4/1994 Sakamoto et al. .............. 435/14
5,589,347 * 12/1996 Arai et al. ...................... 435/11

* cited by examiner

*Primary Examiner*—Louise N. Leary
(74) *Attorney, Agent, or Firm*—Reed Smith LLP

(57) ABSTRACT

An analytical element for quantitative analysis of glucose, cholesterol, or lactic acid in whole blood, composed of a porous layer which has a void volume of 30 to 80% and containing peroxidase, a leuco dye which gives coloring having an absorption peak in the region of 600 to 700 nm, and an oxidase such as glucose oxidase, cholesterol oxidase, or lactate oxidase, respectively. The porous layer can be placed on a transparent support sheet via an adhesive layer in the form of dots or lines, or a hydrophilic adhesive layer.

18 Claims, 5 Drawing Sheets

ANALYTICAL ELEMENT FOR THE ANALYSIS OF WHOLE BLOOD

FIELD OF THE INVENTION

This invention relates to an analytical element for the analysis of glucose, cholesterol or lactic acid in a whole blood sample, and an analytical method using the same. In particular, the invention relates to an analytical element in which an oxidase reaction system produces hydrogen peroxide to give coloring upon reaction with an analyte.

BACKGROUND OF THE INVENTION

The quantitative analyses of analytes such as glucose, cholesterol and lactic acid (or lactate) in a whole blood sample give useful information for diagnosis and treatment of various deceases. In the analyses of these analytes, a dry analytical method utilizing a oxidase reaction system which produces hydrogen peroxide is generally employed. The dry analytical method is performed using an analytical element in the form of a film or a sheet which contains one or more reagents which react with an analyte to show coloring in the element. The dry analytical element is generally held in a mount.

The dry analytical method is advantageous over a wet analytical method from the view points of handling and rapidity in the analytical procedures. However, if a whole blood per se is used as a sample solution for the analysis, the use of a dry analytical element encounters a problem due to the presence of hematocytes (i.e., blood corpuscles) and other solid polymeric components in the blood. In more detail, when the whole blood is spotted on the analytical element, the hematocytes and other solid components are plugged in the element, and there fore a certain portion of the spotted whole blood is not accepted by the element to lower accuracy of the analysis. Further, the plugged hematocytes adversely influence the colorimetry, that is, coloration of hematocytes disturbs measurement of coloring caused by the analytical reaction. In order to solve these problems, hematocytes and other solid components are removed in advance of the analysis, or a spreading layer capable of receiving the hematocytes therein is arranged on the analytical element in the form of an outermost layer.

Japanese Patent Provisional Publication No. 60-82859 discloses a multilayer analytical element comprising a transparent (i.e., light-transmissive) support, an indicator layer containing a dye-forming composition and peroxidase, an oxidase-containing layer, an oxygen-permeable, protein-impermeable, light-shielding layer, and a porous spreading layer, in order. In the analytical element, the dye-forming composition is a composition of 4-aminoantipyrine and its coupler (i.e., 1,7-dihydroxy-naphthalene), and the porous spreading layer is made of 100% cotton broadcloth. The light-shielding layer shields red color of hemoglobin from the coloring produced by the analytical reaction and further functions as a light-reflecting layer. The analytical element disclosed in the publication has an oxidase-containing layer or a mordant layer containing oxidase between the indicator layer and the light-shielding layer. This arrangement enables to obviate lowering of analytical accuracy caused by hydrogen peroxidase-decomposing components in the whole blood, such as catalase. It is known that oxidase functions satisfactorily under enough supply of airy oxygen. Therefore, the desired rapid analysis cannot be expected because the oxidase-containing layer cannot receive enough airy oxygen supply due to the presence of the light-shielding layer and spreading layer placed on the oxidase-containing layer.

Japanese Patent Publication No. 60-111960 discloses a multilayer analytical element for the analysis of whole blood which has no filter layer, that is no spreading layer. The analytical element has, on a light-transmissive support sheet, a recording zone comprising gelatin and a reagent-coated zone in order. The reagent-coated zone is a coated layer comprising beads, oxidase, peroxidase, and a color-forming composition of 4-aminoantipyrine and its coupler. The reagent-coated zone of the analytical element shows high light-shielding power. In the analytical procedures, a dye produced in the reagentcoated zone is transferred into the recording zone (i.e., gelatin layer) and then measured by colorimetry at a wavelength of 600 nm or longer. A color produced by the reaction of 4-aminoantipyrine and its coupler varies depending upon the selection of coupler. For instance, the use of 8-anilino-1-naphthalenesulfonic acid as the coupler gives a dye having a absorption area at 600 nm or longer wavelength. The calorimetric measurement at a wavelength of 600 nm or longer enable to remove the adverse effect of the colored solid components in the whole blood. However, the transfer of the produced dye is accompanied by diffusion of the dye, so that the analytical accuracy lowers.

Japanese Patent Provisional Publication No. H4-324347 describes a whole-blood analyzing element having a plural number of oxygen-supplying holes so as to increase the oxygen supply. The analyzing element may or may not have a light-transmissive support and has no lightshielding layer. The dye-forming composition comprises 4-aminoantipyrine and its coupler, but the calorimetric measurement is carried out at a wavelength of 541 nm. Therefore, the disturbance by the red color of whole blood is not completely obviated, and the dye-forming reaction (i.e., color-forming reaction) does not proceed rapidly.

Japanese Patent Provisional Publication No. H9-121894 discloses a whole blood-analyzing strip comprising an anisotropic film which contains an acrylic polymer having low reactivity to the hematocrit in whole blood. This strip has a disadvantage in that satisfactory uniform distribution of the spotted whole blood in the lateral direction is not attained.

SUMMARY OF THE INVENTION

It is an object of the present invention to provide an analytical element employable for rapid quantitative analysis of glucose, cholesterol, or lactic acid (or lactate) present in a whole blood sample with almost no adverse effect of hematocytes in the whole blood sample.

More specifically, the object of the invention is to provide an analytical element which has no hematocyte-filtering layer but which is employable for rapid quantitative analysis of glucose, cholesterol, or lactic acid present in a whole blood sample with almost no adverse effect of hematocytes in the blood sample.

The present invention further has an object to provide a method for quantitatively analyzing glucose, cholesterol, or lactic acid in a whole blood sample.

The present invention resides in an analytical element for quantitative analysis of glucose, cholesterol, or lactic acid in a whole blood sample, consisting essentially of a porous layer which has a void volume of 30 to 80% and containing peroxidase, a leuco dye which gives coloring having an absorption peak in the region of 600 to 700 nm, and an oxidase selected from the group consisting of glucose oxidase, cholesterol oxidase and lactate oxidase, respectively.

The invention also resides in a multilayer analytical element for quantitative analysis of glucose, cholesterol, or lactic acid in a whole blood sample, consisting essentially of a light-transmissive support sheet and a porous layer which has a void volume of 30 to 80% and containing peroxidase, a leuco dye which gives coloring having an absorption peak in the region of 600 to 700 nm, and an oxidase selected from the group consisting of glucose oxidase, cholesterol oxidase and lactate oxidase, respectively, said support sheet and porous layer being combined to each other with an adhesive layer in the form of dots or lines.

The invention further resides in a multilayer analytical element for quantitative analysis of glucose, cholesterol, or lactic acid in a whole blood sample, consisting essentially of a light-transmissive support sheet, a hydrophilic adhesive layer, and a porous layer which has a void volume of 30 to 80% and containing peroxidase, a leuco dye which gives coloring having an absorption peak in the region of 600 to 700 nm, and an oxidase selected from the group consisting of glucose oxidase, cholesterol oxidase and lactate oxidase, respectively, said adhesive layer being placed between the support sheet and porous layer.

The invention further resides in a method for quantitatively analyzing glucose, cholesterol, or lactic acid in a whole blood sample, which comprises spotting the whole blood sample on an analytical element of the invention and measuring coloring appearing in the analytical element.

DETAILED DESCRIPTION OF THE INVENTION

Preferred embodiments of the invention are described below:

1) The porous layer of the analytical element is made of knitted fabric.

2) The porous layer of the analytical element has a thickness of 50 to 300 μm and contains the leuco dye in an amount of 1 to 10 g/m$^2$.

The invention is further described by referring to the figures illustrated in the attached drawings.

Figure 1:
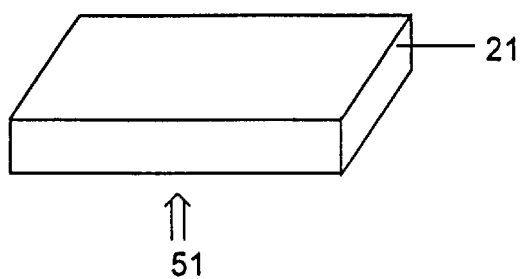
FIG. 1 schematically illustrates an analytical element (A) according to the invention.

FIG. 1 shows an analytical element (A) consisting of a porous layer 21 which has a void volume of 30 to 80% and containing peroxidase, a leuco dye which gives coloring having an absorption peak in the region of 600 to 700 nm, and such an oxidase as glucose oxidase, cholesterol oxidase, or lactate oxidase.

Figure 2:
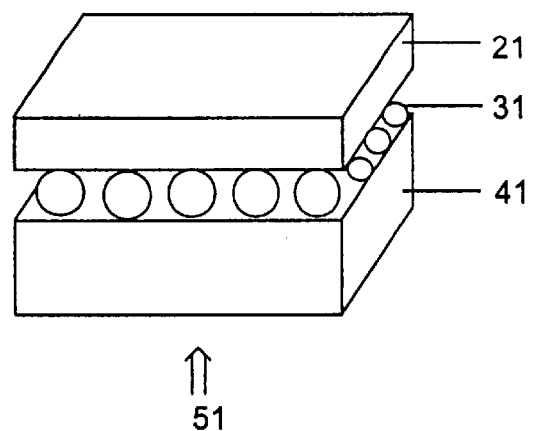
FIG. 2 schematically illustrates a multilayer analytical element (B) according to the invention.

FIG. 2 shows a multilayer analytical element (B) which is improved in handling characteristics and which consists of a light-transmissive support sheet 41 and a porous layer 21 which has a void volume of 30 to 80% and containing peroxidase, a leuco dye which gives coloring having an absorption peak in the region of 600 to 700 nm, and such an oxidase as glucose oxidase, cholesterol oxidase, or lactate oxidase, in which the support sheet and porous layer are combined to each other with an adhesive layer 31 in the form of dots or lines.

Figure 3:
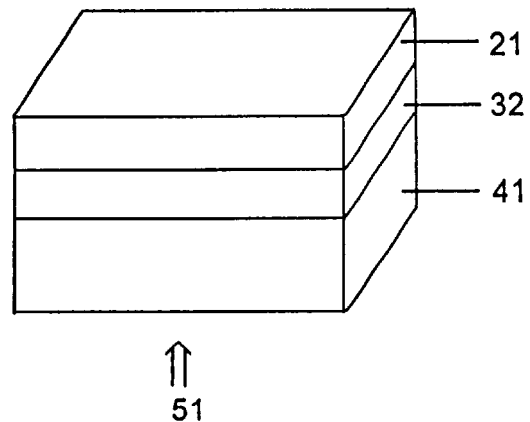
FIG. 3 schematically illustrates a multilayer analytical element (C) according to the invention.

FIG. 3 shows a multilayer analytical element (C) consisting of a light-transmissive support sheet 41, a hydrophilic adhesive layer 32, and a porous layer 21 which has a void volume of 30 to 80% and containing peroxidase, a leuco dye which gives coloring having an absorption peak in the region of 600 to 700 nm, and such an oxidase as glucose oxidase, cholesterol oxidase, or lactate oxidase, in which the adhesive layer 32 is placed between the support sheet 41 and porous layer 21.

All of the analytical elements (A), (B), and (C) according to the invention has no oxygen-permissible, protein-impermeable, light-shielding layer disclosed in the aforementioned Japanese Patent Provisional Publication No. 60-82859.

The analytical element of the invention is further described below.

The porous layer is a porous reagent layer which has a void volume of 30 to 80% and contains peroxidase, a leuco dye which gives coloring having an absorption peak in the region of 600 to 700 nm, and such an oxidase as glucose oxidase, cholesterol oxidase, or lactate oxidase. The porous reagent layer is produced by coating the reagent composition on a porous sheet having a void volume of 30 to 80%. The porous sheet can be immersed in a solution of the reagent composition to give the porous reagent layer.

The porous reagent layer preferably has a thickness in the range of 1 to 500 μm, preferably in the range of 5 to 300 μm.

The porous sheet having a void volume of 30 to 80% can be a fabric sheet or a non-fabric sheet. The fabric sheet can be a sheet of textile fabric, knitted fabric, non-woven fabric, filter paper, or agglomerated short fibers. The non-fabric sheet typically is a membrane filter. A sheet of diatomaceous particles dispersed in a binder may be employed. A sheet of glass beads or resin particles bonded together by adhesive is also employable. Preferred is a fabric sheet having a void volume of 30 to 80%, preferably 50 to 70%. A knitted fabric is most preferred.

The knitted fabric can be plain knitted fabric, tricot knitted fabric, double tricot knitted fabric, or milanese tricot fabric. The fibrous material for forming the knitted fabrics can be of natural origin such as cotton, kapok, flax, hemp, ramie, silk or wool, or of synthetic origin such as polyamide, polyester, rayon, cupra, cellulose acetate, polyvinyl alcohol, polyacrylate, or polyethylene terephthalate. These fibrous materials can be employed in combination. The thickness of the fibrous material preferably is in the range of 10 to 80 denier.

Glucose oxidase preferably originates from *Aspergillus niger* or *Penicillium notatum*.

Cholesterol oxidase preferably originates from *Nocardia erythroporis*, Brevibacterium, Pseudomonas, Mycobacterium, or mushrooms.

Lactate oxidase preferably originates from *Aerococcus viridans*, or *Pediococcus sp*.

Each of glucose oxidase, cholesterol oxidase and lactate oxidase is preferably contained in the porous reagent layer in an amount of 2,000 to 40,000 U/m$^2$, more preferably 4,000 to 30,000 U/m$^2$.

Peroxidase can be of plant origin, animal origin, or microorganism origin. Preferred are peroxidases of plant origin and microorganism origin. Most preferred are peroxidase extracted from horseradish or Japanese radish, and peroxidase extracted from microorganisms of genus Cochlibolus or genus Curvularia.

Peroxidase is preferably contained in the porous reagent layer in an amount of 5,000 to 100,000 $U/m^2$, more preferably 10,000 to 60,000 $U/m^2$.

The leuco dye gives coloring under catalytic action of an oxidizing compound such as peroxidase in the presence of hydrogen peroxide. Examples of the leuco dyes are described in Japanese Patent Provisional Publication No. 59-193352. The leuco dyes described in the publication produce blue color having an absorption peak of 600 nm or longer, specifically in the region of 600 to 700 nm. Preferred leuco dyes are 2-(3,5-dimethoxy-4-hydroxyphenyl)-4-[4-(dimethylamino)phenyl]-5-phenethylimidazole and 2-(3,5-dimethoxy-4-hydroxyphenyl)-4-[4-(dimethylamino)phenyl]-5-benzylimidazole.

The leuco dye is preferably contained in the porous reagent layer in an amount of 0.1 to 10 $g/m^2$ more preferably 1 to 10 $g/m^2$. Such a small amount of the leuco dye required in the analytical element of the invention is advantageous over the known.

The porous layer further can contain other additives such as a pH-adjusting agent and a surface active agents.

The pH-adjusting agent is selected to maintain an optimum pH condition for the enzyme composition (a combination of oxidase and peroxidase). Preferred pH-adjusting agents are phosphate buffers, citrate buffers, borate buffers, Tris buffer, and Good's buffer.

The surface active agents functions to make the porous reagent layer hydrophilic so as to accelerate the reaction between the leuco dye and hydrogen peroxide in the layer.

Examples of the surface active agents are watersoluble nonionic, cationic, anionic, and amphoteric surface active agents. Examples of the nonionic surface active agents include dimethylcyclohexane/methyl(polyoxyethylene) copolymer, alkylaryl ethers of polyoxyethylene or polyglycerql, and fatty acid esters. A nonionic surface active agent having 8 to 15 oxyethylene or oxypropylene units is most preferred.

Each of the aforementioned analytical elements (B) and (C) (illustrated in FIGS. 2 and 3, respectively) has a light-transmissive support sheet in addition to the porous reagent layer, in which the support sheet and the porous reagent are combined to each other with an adhesive layer preferably comprising a hydrophilic adhesive.

Examples of the adhesives can be natural products, inorganic materials, thermo-setting resins, thermoplastic resins, elastic resins, pressure-sensitive adhesives, hot-melt adhesives, cyanoacrylate adhesives, and other known adhesives.

The multilayer analytical element (B) is preferably manufactured using a hot-melt adhesive. The hot-melt adhesive is a solid adhesive (i.e., solid at room temperature) consists mainly of thermoplastic resin. The hotmelt adhesive is melted in a heated applicator and spotted on the support sheet in the form of dots, lines, or their combinations. Thus formed non-continuous adhesive layer serves to efficiently supply airy oxygen into the porous reagent layer. The adhesive layer preferably has a thickness in the range of 5 to 100 $\mu$m, more preferably 10 to 30 $\mu$m.

The multilayer analytical element (C) is manufactured by coating a hydrophilic adhesive on the whole surface of the support sheet. Preferably, on the hydrophilic adhesive layer, a surface active agent such as that described hereinbefore is coated. Thus formed continuous hydrophilic adhesive layer also serves to efficiently supply airy oxygen into the porous reagent layer. The continuous adhesive layer preferably has a thickness in the range of 5 to 100 $\mu$m, more preferably 10 to 30 $\mu$m.

Employable adhesives are described in Japanese Patent Provisional Publications No. 55-164356 and No. 57-208997. Examples of the adhesives include gelatin, gelatin derivatives, pullulan, pullulan derivatives, agarose, polyvinyl alcohol, polyvinyl pyrrolidone, and polyacrylamide. Gelatin is preferred.

The light-transmissive support sheet is a non-water permissible transparent support sheet. The light-transmissive support sheet employable in the analytical element of the invention may be one of those described in Japanese Patent Provisional Publication No. 55-164356. Examples of the materials for producing the support sheet are hydrophobic or nearly hydrophobic polymers such as polyethylene terephthalate, cellulose acetate, polycarbonate of bisphenol A, polystyrene, and polymethyl methacrylate. A transparent glass plate is also employable. Preferred is a polyethylene terephthalate sheet. The support sheet preferably has a thickness of 50 $\mu$m to 1 mm, more preferably 80 to 400 $\mu$m, in the case of a polymer sheet, while it preferably has a thickness of 100 $\mu$m to 2 mm, more preferably 150 $\mu$m to 1 mm, in the case of a glass plate.

The surface of the support sheet can be treated by known physical or chemical surface activating treating methods such as treatments with ultraviolet rays, corona discharge, and glow discharge, so as to have increased adhesion with the adhesive layer. Further, in addition to the physical or chemical surface activation or independently, a gelatin-subbing layer can be placed on the support sheet.

The analytical method of the invention can be performed by spotting a whole blood sample on an analytical element of the invention, incubating the spotted element, if necessary, and measuring calorimetrically an optical density (i.e., color density) of a color or color change produced on the analytical element at a wavelength in the region of 600 to 700 nm. The calorimetric measurement is performed by applying the measuring light onto the light-transmissive support sheet (arrow 51 in FIGS. 2 and 3) in the case of using the analytical element (B) or (C). In the case of using the analytical element (A), the calorimetric measurement can be performed on either surface side. So long as the measurement is done at a wavelength in the specified range, almost no adverse effect by erythrocyte supplied with the whole blood sample is observed. The optimum wavelength for the measuring light may vary depending on the natures of leuco dyes. The whole blood sample is preferably spotted in an amount of 1 to 10 $\mu$L.

The calorimetric measurement in the analytical method of the invention is performed by directly detecting color of the dye produced in the porous reagent layer. Thus, the color of the produced dye is measured in situ, and the dye does not diffuse. Accordingly, no decrease of analytical accuracy caused by the dye diffusion occurs in the analytical method utilizing the analytical element of the invention.

The analytical element of the invention is generally held in a mount (i.e., holder) in the manner described in Japanese Patent Provisional Publication No. 57-63452. The mount may be produced from polyethylene, polypropylene, polyvinyl chloride, polystyrene, polyamide, polycarbonate, polyethylene terephthalate, ABS resin, polymethyl methacrylate (PMMA) resin, ceramics (e.g., alumina and silica), or metals (e.g., aluminum, stainless steel, or titanium).

The present invention is further described by the following examples.

EXAMPLE 1

(1) Preparation of Analytical Element

On a tricot knitted fabric (void volume: 60%, thickness: approx. 250 μm, produced by knitting polyethylene terephthalate yarn of 50 denier to give 36 gauge structure) was coated an aqueous solution of glucose oxidase (30,000 U/m$^2$), peroxidase (10,000 U/m$^2$), 2-(3,5-dimethoxy-4-hydroxyphenyl)-4-[4-(dimethylamino)phenyl]-5-phenethyl imidazole acetate (3 g/m$^2$), nonylphenoxypolyethoxyethanol (number of oxyethylene unit: average 9 to 10, 0.15 g/m$^2$), 2-morpholinoethanesulfonic acid (MES, 1 g/m$^2$), and ion-exchanged water (180 g). The coated fabric was dried at 50° C. to give a porous reagent sheet.

(2) Manufacture of Analytical Slide

The porous reagent sheet prepared above (i.e., analytical element of the invention) was cut to give square chips (12 mm ×13 mm) and mounted in a slide frame (described in Japanese Patent Provisional Publication No. 57-63452), to give a GLU-W dry analytical slide (I) for analyzing a whole blood sample to quantitatively measure the amount of glucose.

(3) Analytical Procedures

To a human whole blood was added an aqueous solution of glucose in ion-exchanged water to prepare two aqueous samples having different glucose concentrations, namely, 200 mg/dL and 600 mg/dL. On the GLU-W analytical slide was spotted 6 μm of each aqueous sample separately. The progress of color formed in the analytical slide was continuously measured at 650 nm using Fuji Drychem 5000 (available from Fuji Photo Film Co., Ltd.).

Figure 5:
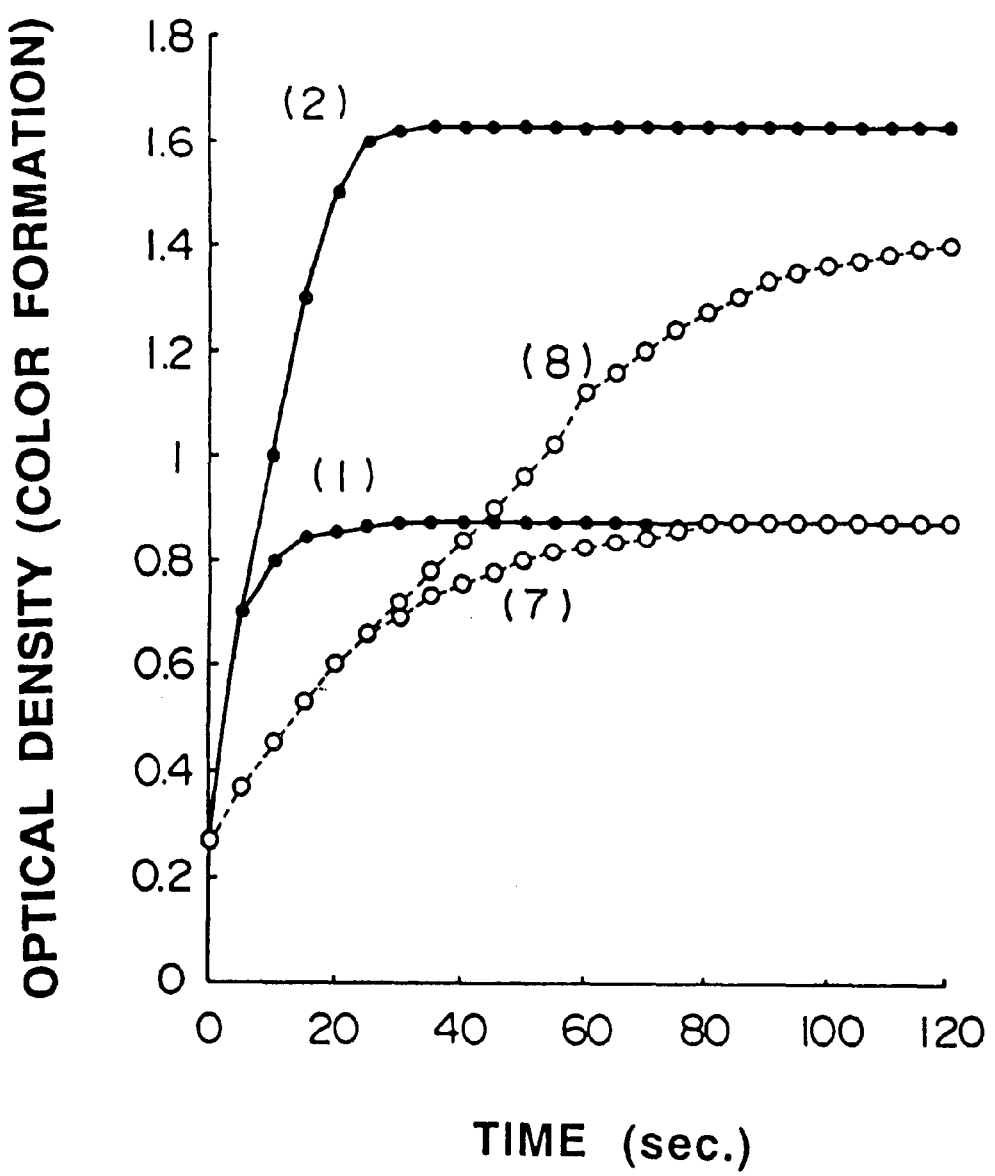
FIG. 5 graphically shows results of Example 1 and Comparison Example 1.

The results of the measurement are graphically shown in FIG. 5. The curve (1) is for the progress of the color formation observed in the measurement using the 200 mg/dL sample, and the curve (2) is for the progress of the color formation observed in the measurement using the 600 mg/dL sample.

EXAMPLE 2

(1) Preparation of Analytical Element

On a tricot knitted fabric (void volume: 60%, thickness: approx. 250 μm, produced by knitting polyethylene terephthalate yarn of 50 denier to give 36 gauge structure) was coated an aqueous solution of glucose oxidase (30,000 U/m$^2$), peroxidase (10,000 U/m$^2$), 2-(3,5-dimethoxy-hydroxyphenyl)-4-[4-(dimethylamino)phenyl]-5-phenethylimidazole acetate (3 g/m$^2$), nonylphenoxypolyethoxyethanol (number of oxyethylene unit: average 9 to 10, 0.15 g/m$^2$), 2-morpholinoethanesulfonic acid (MES, 1 g/m$^2$), and ionexchanged water (180 g). The coated fabric was dried at 50° C. to give a porous reagent sheet.

A hot melt adhesive was melted by heating to 130° C. The melted adhesive was printed in the form of dots using a gravure roll on a colorless transparent polyethylene terephthalate sheet (support sheet, thickness: 180 μm) in an amount of 3 g/m$^2$. The gravure roll had a pattern of dots having a size of 0.3 mm (diameter), a distance between the centers of adjacent dots of 0.6 mm, and a dot area ratio of 20%. On the adhesive formed on the support sheet, the porous reagent sheet produced above was fixed using a laminating roller to give a multilayer analytical element of the invention.

(2) Manufacture of Analytical Slide

The multilayer analytical element prepared above was cut to give square chips (12 mm ×13 mm) and mounted in a slide frame in the same manner as in Example 1, to give a GLU-W dry analytical slide (II) for analyzing a whole blood sample to quantitatively measure the amount of glucose.

(3) Analytical Procedures

The analytical procedures of Example 1 were repeated except for employing the GLU-W analytical slide (II) in place of the GLU-W analytical slide (I).

Figure 6:
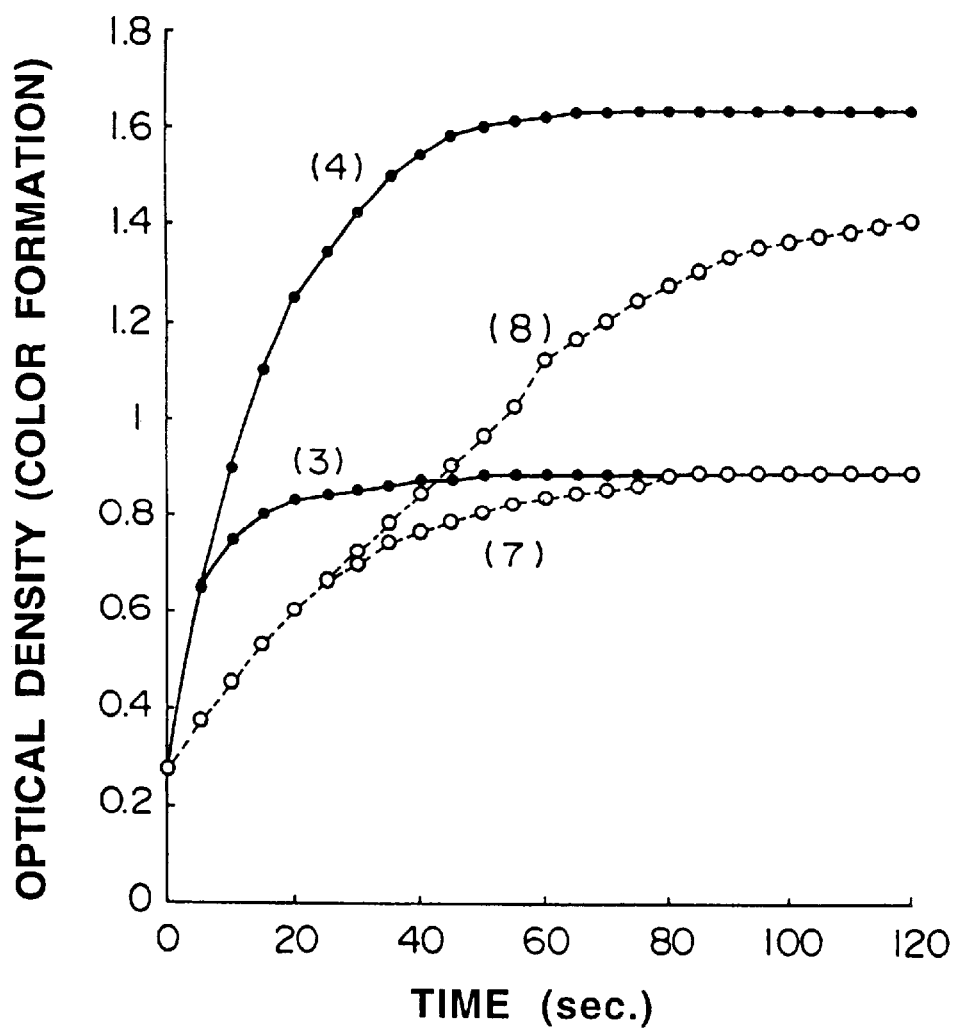
FIG. 6 graphically shows results of Example 2 and Comparison Example 1.

The results of the measurement are graphically shown in FIG. 6. The curve (3) is for the progress of the color formation observed in the measurement using the 200 mg/dL sample, and the curve (4) is for the progress of the color formation observed in the measurement using the 600 mg/dL sample.

EXAMPLE 3

(1) Preparation of Analytical Element

An aqueous solution of alkali-treated gelatin in ion-exchanged water was coated on a colorless transparent polyethylene terephthalate sheet (support sheet, thickness: 180 μm) in an amount of 8.0 g/m$^2$. The coated solution was dried at 50° C. to give an adhesive layer.

On the adhesive layer formed on the support sheet, an aqueous solution of nonylphenoxypolyethoxyethanol (number of oxyethylene unit: average 9 to 10) was coated in an amount of 0.15 g/m$^2$ to wet the adhesive gelatin layer. On the wet adhesive layer was placed a tricot knitted fabric (void volume: 60%, thickness: approx. 250 μm, produced by knitting polyethylene terephthalate yarn of 50 denier to give 36 gauge structure) under light pressure to fix the fabric onto the support sheet.

On the fixed fabric was coated an aqueous solution of glucose oxidase (30,000 U/m$^2$), peroxidase (10,000 U/m$^2$), 2-(3,5-dimethoxy-4-hydroxyphenyl)-4-[4-(dimethylamino) phenyl]-5-phenethylimidazole acetate (3 g/m$^2$), 2-morpholinoethanesulfonic acid (MES, 1 g/m$^2$), and ion-exchanged water (180 g). The coated fabric was dried at 50° C. to give a porous reagent layer. Thus, a multilayer analytical element of the invention was prepared.

(2) Manufacture of Analytical Slide

The multilayer analytical element prepared above was cut to give square chips (12 mm ×13 mm) and mounted in a slide frame in the same manner as in Example 1, to give a GLU-W dry analytical slide (III) for analyzing a whole blood sample to quantitatively measure the amount of glucose.

(3) Analytical Procedures

The analytical procedures of Example 1 were repeated except for employing the GLU-W analytical slide (III) in place of the GLU-W analytical slide (I).

Figure 7:
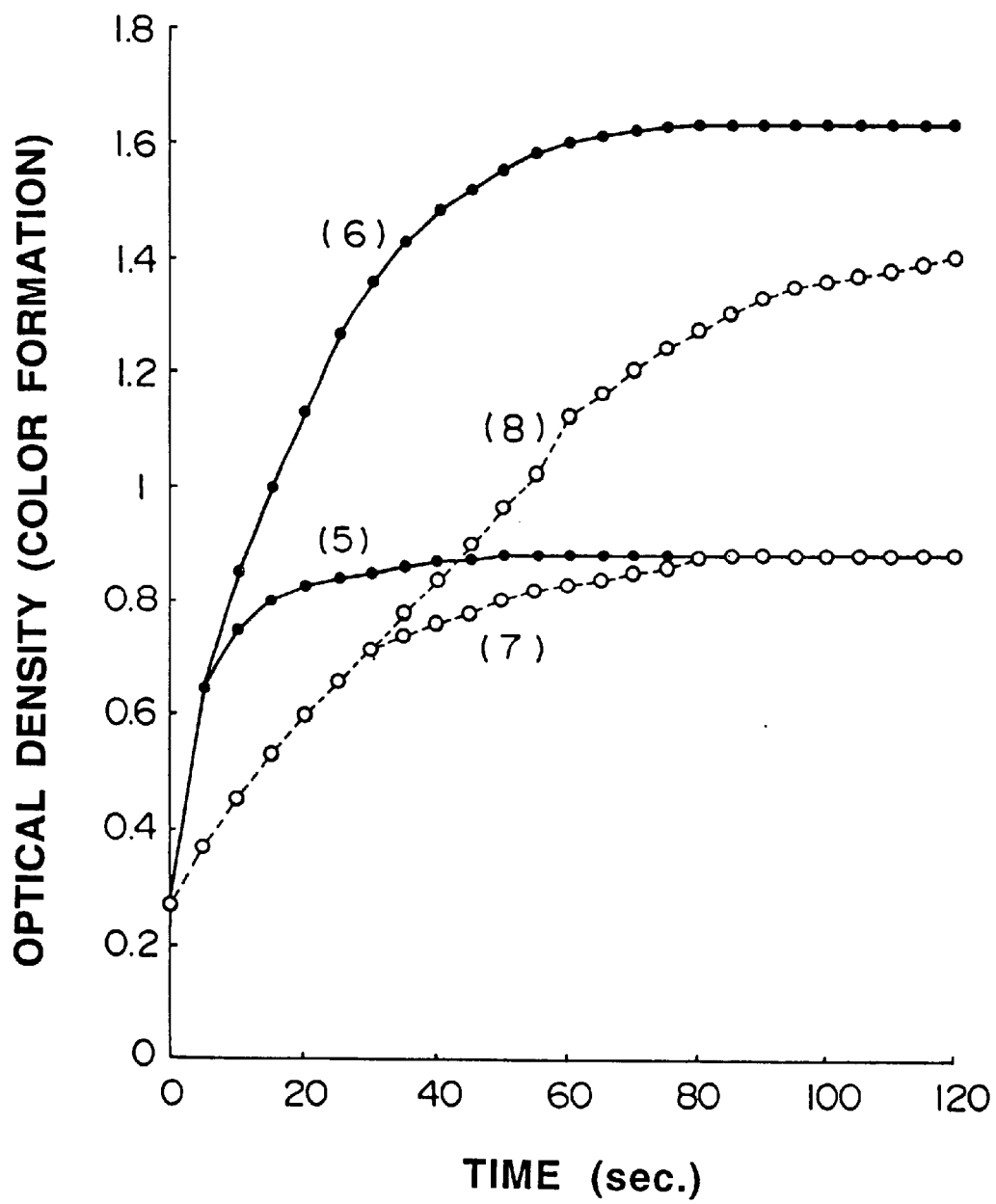
FIG. 7 graphically shows results of Example 3 and Comparison Example 1.

The results of the measurement are graphically shown in FIG. 7. The curve (5) is for the progress of the color formation observed in the measurement using the 200 mg/dL sample, and the curve (6) is for the progress of the color formation observed in the measurement using the 600 mg/dL sample.

COMPARISON EXAMPLE 1

(1) Preparation of Analytical Element

On a colorless transparent polyethylene terephthalate sheet (support sheet, thickness: 180 μm) having a gelatin subbing layer was coated an aqueous solution of alkali-treated gelatin (20 g/m$^2$), nonlylphenoxypolyethoxyehtanol (number of oxyethylene unit: average 9 to 10, 0.2 g/m$^2$), peroxidase (10,000 U/m$^2$), glucose oxidase (10,000 U/m$^2$), 2-[(4-hydroxy-3,5-dimethoxy)phenyl]-4-(4-dimethylamino) phenyl]-5-phenethylimidazole acetate (0.3 g/m$^2$), 2-morpholinoethanesulfonic acid (MES, 1 g/m$^2$), and ion-exchanged water (180 g). The coated solution was dried at 50° C. to give a reagent layer.

On the reagent layer was coated an aqueous solution of nonlylphenoxypolyethoxyehtanol (number of oxyethylene unit: average 9 to 10) in an amount of 0.15 g/m$^2$ in ionexchanged water in an amount of 30 g/m$^2$, to wet the surface of the reagent layer. Thereafter, the wet reagent layer was dried at 50° C.

Figure 4:
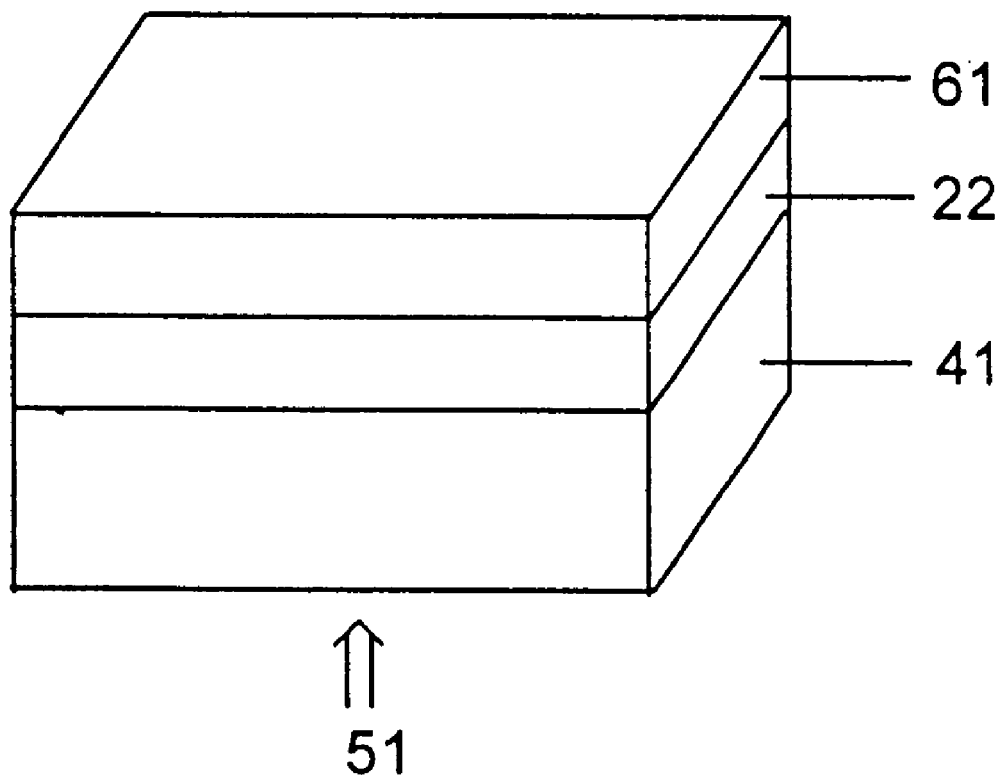
FIG. 4 schematically illustrates a known multilayer analytical element for comparison.

On the reagent layer formed on the support sheet was placed a tricot knitted fabric (void volume: 60%, thickness: approx. 250 μm, produced by knitting polyethylene terephthalate yarn of 50 denier to give 36 gauge structure) under light pressure to fix the fabric onto the support sheet. Thus, a multilayer analytical element for comparison (illustrated in FIG. 4) was prepared.

(2) Manufacture of Analytical Slide

The multilayer analytical element prepared above was cut to give square chips (12 mm ×13 mm) and mounted in a slide frame in the same manner as in Example 1, to give a GLU-W dry analytical slide (IV) for analyzing a whole blood sample to quantitatively measure the amount of glucose.

(3) Analytical Procedures

The analytical procedures of Example 1 were repeated except for employing the GLU-W analytical slide (IV) in place of the GLU-W analytical slide (I).

The results of the measurement are graphically shown in FIG. 5. The curve (7) is for the progress of the color formation observed in the measurement using the 200 mg/dL sample, and the curve (8) is for the progress of the color formation observed in the measurement using the 600 mg/dL sample.

Evaluation of Analytical Element

FIG. 5 indicates that the color formation reaction (coloring) is complete within a short period such as shorter than approx. 20 seconds when the analytical slide (I) of the invention is used. Further, FIGS. 6 and 7 indicate that the color formation reactions are complete within a short period such as approx. 50 seconds and 60 seconds, respectively, when the analytical slide (II) and the analytical slide (III) of the invention are used.

In contrast, the color formation reaction in the known analytical slide (VI) requires an apparently longer period such as more than 120 seconds for the completion of reaction.

What is claimed is:

1. An analytical element for quantitative analysis of glucose, cholesterol, or lactic acid in a whole blood sample, consisting essentially of a porous layer which has a void volume of 30 to 80% and containing peroxidase, a leuco dye which gives coloring having an absorption peak in the region of 600 to 700 nm, and an oxidase selected from the group consisting of glucose oxidase, cholesterol oxidase and lactate oxidase, respectively.

2. A multilayer analytical element for quantitative analysis of glucose, cholesterol, or lactic acid in a whole blood sample, consisting essentially of a light-transmissive support sheet and a porous layer which has a void volume of 30 to 80% and containing peroxidase, a leuco dye which gives coloring having an absorption peak in the region of 600 to 700 nm, and an oxidase selected from the group consisting of glucose oxidase, cholesterol oxidase and lactate oxidase, respectively, said support sheet and porous layer being combined to each other with an adhesive layer in the form of dots or lines.

3. A multilayer analytical element for quantitative analysis of glucose, cholesterol, or lactic acid in a whole blood sample, consisting essentially of a light-transmissive support sheet, a hydrophilic adhesive layer, and a porous layer which has a void volume of 30 to 80% and containing peroxidase, a leuco dye which gives coloring having an absorption peak in the region of 600 to 700 nm, and an oxidase selected from the group consisting of glucose oxidase, cholesterol oxidase and lactate oxidase, respectively, said adhesive layer being placed between the support sheet and porous layer.

4. The analytical element of claim 1, wherein the porous layer is made of knitted fabric.

5. The analytical element of claim 2, wherein the porous layer is made of knitted fabric.

6. The analytical element of claim 3, wherein the porous layer is made of knitted fabric.

7. The analytical element of claim 1, wherein the porous layer has a thickness of 50 to 300 μm and contains the leuco dye in an amount of 1 to 10 g/m$^2$.

8. The analytical element of claim 2, wherein the porous layer has a thickness of 50 to 300 μm and contains the leuco dye in an amount of 1 to 10 g/m$^2$.

9. The analytical element of claim 3, wherein the porous layer has a thickness of 50 to 300 μm and contains the leuco dye in an amount of 1 to 10 g/m$^2$.

10. A method for quantitatively analyzing glucose, cholesterol, or lactic acid in a whole blood sample, which comprises spotting the whole blood sample on an analytical element and measuring coloring appearing in the analytical element, said analytical element consisting essentially of a porous layer which has a void volume of 30 to 80% and containing peroxidase, a leuco dye which gives coloring having an absorption peak in the region of 600 to 700 nm, and an oxidase selected from the group consisting of glucose oxidase, cholesterol oxidase and lactate oxidase, respectively, and the measurement of coloring being made at a wavelength in the range of 600 to 700 nm.

11. A method for quantitatively analyzing glucose, cholesterol, or lactic acid in a whole blood sample, which comprises spotting the whole blood sample on a multilayer analytical element and measuring coloring appearing in the analytical element, said analytical element consisting essentially of a light-transmissive support sheet and a porous layer which has a void volume of 30 to 80% and containing peroxidase, a leuco dye which gives coloring having an absorption peak in the region of 600 to 700 nm, and an oxidase selected from the group consisting of glucose oxidase, cholesterol oxidase and lactate oxidase, respectively, wherein the support sheet and porous layer is combined to each other with an adhesive layer in the form of dots or lines, and the measurement of coloring being made at a wavelength in the region of 600 to 700 nm.

12. A method for quantitatively analyzing glucose, cholesterol or lactic acid in a whole blood sample, which comprises spotting the whole blood sample on a multilayer analytical element and measuring coloring appearing in the analytical element, said analytical element consisting essentially of a light-transmissive support sheet, a hydrophilic adhesive layer, and a porous layer which has a void volume of 30 to 80% and containing peroxidase, a leuco dye which gives coloring having an absorption peak in the region of 600 to 700 nm, and an oxidase selected from the group consisting of glucose oxidase, cholesterol oxidase and lactate oxidase, respectively, wherein the adhesive layer is placed between the support sheet and porous layer, and the measurement of coloring being made at a wavelength in the region of 600 to 700 nm.

13. The analytical method of claim 10, wherein the porous layer of the analytical element is made of knitted fabric.

14. The analytical method of claim 11, wherein the porous layer of the analytical element is made of knitted fabric.

15. The analytical method of claim 12, wherein the porous layer of the analytical element is made of knitted fabric.

16. The analytical method of claim 10, wherein the porous layer of the analytical element has a thickness of 50 to 300 μm and contains the leuco dye in an amount of 1 to 10 g/m$^2$.

17. The analytical method of claim 11, wherein the porous layer of the analytical element has a thickness of 50 to 300 μm and contains the leuco dye in an amount of 1 to 10 g/m$^2$.

18. The analytical method of claim 12, wherein the porous layer of the analytical element has a thickness of 50 to 300 μm and contains the leuco dye in an amount of 1 to 10 g/m$^2$.

* * * * *